United States Patent [19]

Kino et al.

[11] 4,325,257

[45] Apr. 20, 1982

[54] REAL-TIME DIGITAL, SYNTHETIC-FOCUS, ACOUSTIC IMAGING SYSTEM

[76] Inventors: Gordon S. Kino, 867 Cedro Way; Paul D. Corl, 53-D Escondido Village, both of Stanford, Calif. 94305; Peter M. Grant, #9 Grange Rd., Edinburgh, Scotland, EH9 1U.Q.

[21] Appl. No.: 122,880

[22] Filed: Feb. 20, 1980

[51] Int. Cl.³ ............................................. G01N 29/00
[52] U.S. Cl. ...................................... 73/626; 73/632; 364/604; 364/724
[58] Field of Search ................. 73/626, 625, 628, 631, 73/632; 364/724, 725, 726, 728, 602, 604, 606, 825, 826, 827; 367/105; 310/334, 335, 336; 128/660

[56] References Cited

U.S. PATENT DOCUMENTS

| | | | |
|---|---|---|---|
| 3,891,869 | 6/1975 | Scarpa | 310/334 |
| 4,120,035 | 10/1978 | Cases et al. | 364/825 |
| 4,127,034 | 11/1978 | Lederman et al. | 73/626 |
| 4,211,949 | 7/1980 | Brisken et al. | 310/336 |

OTHER PUBLICATIONS

B. Widrow et al., "Stationary and Nonstationary Learning Characteristics of the LMS Adaptive Filter," *Proceedings of the IEEE*, vol. 64, No. 8, pp. 1151–1162, Aug. 1976.

*Primary Examiner*—Stephen A. Kreitman
*Attorney, Agent, or Firm*—Paul B. Fihe

[57] ABSTRACT

The invention involves a digital synthetic-focus, acoustic imaging system which is operative in real time and includes one or more electro-acoustic transducers arranged to receive broadband pulses from a pulse generator for excitation of acoustic pulses which are directed into the region under observation. Signals reflected from an object or discontinuity in the region are received by the same transducers, and after inverse filtering and nonlinear amplification are converted to digital signals. These digital signals are stored in separate high speed random access memory units for storage, but are subsequently time-equalized through use of a programmed focus memory unit prior to delivery to a digital adder and thence through a digital-to-analog converter for ultimate intensity modulation on a raster scanned display unit which provides the real time image.

4 Claims, 7 Drawing Figures

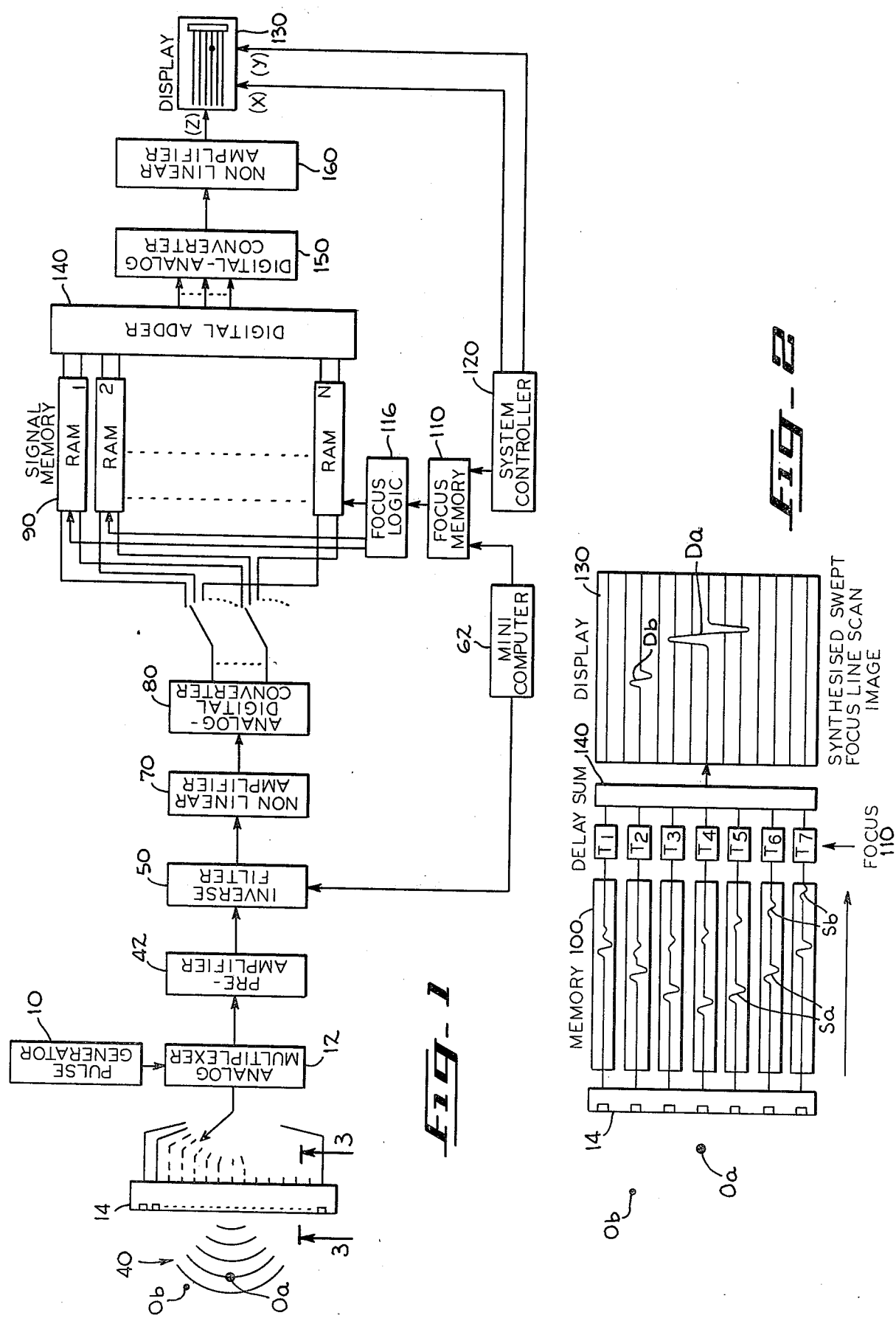

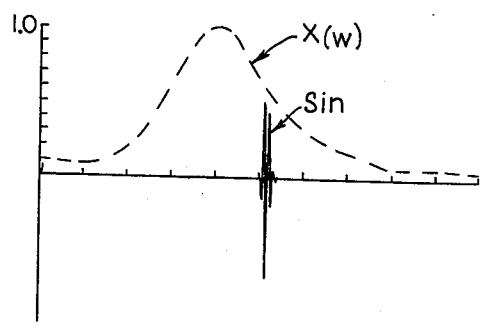
(INPUT SIGNAL)
Fig_6A
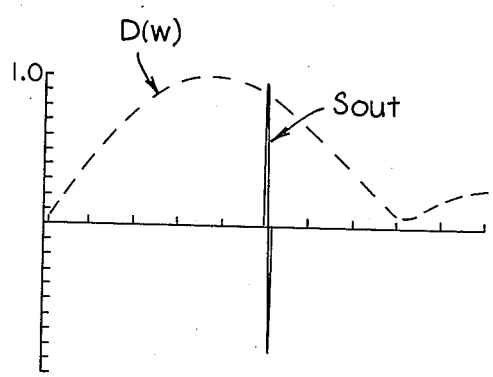
(OUTPUT)
Fig_6B

REAL-TIME DIGITAL, SYNTHETIC-FOCUS, ACOUSTIC IMAGING SYSTEM

FIELD OF THE INVENTION

The present invention relates generally to acoustic imaging techniques, and, more particularly, to a digital, synthetic-focus, acoustic imaging system operative in real time.

BACKGROUND OF THE INVENTION

Since standard optical techniques do not allow the inspection of interior sections, for example of an organ in the human body or stresses or cracks in the interior of a metal or other solid part, alternate techniques including x-ray and radiographic methods, eddy current testing in metals, the use of dye penetrants, and, more recently, utilization of acoustic imaging methods have been employed.

Radiographic techniques require bulky apparatus, particularly for thick metal parts, and high energy beams must be employed so as to require clearing of the area where the inspection is being made.

The eddy current techniques also provide very useful information, but only on near-surface defects in metals; and, in turn, fluorescent dye penetrants provide a simple and effective way of detecting surface defects, but do not necessarily evaluate accurately the depth of the crack or any of its characteristics.

As a consequence, acoustic techniques have been increasingly utilized, as they can readily penetrate the otherwise opaque bodies to measure the subsurface elastic properties of the material. For example, an acoustic microscope has been developed wherein the acoustic energy is focused by a spherical lens and the sample is scanned by means of a loudspeaker movement in one direction and by a hydraulic piston in the perpendicular direction. Such mechanical scanning of a region point by point is relatively slow and provides a major disadvantage of the arrangement.

Some attempts have been made, as a consequence, to provide electronically variable focusing techniques rather than the physical lens, to provide much more rapid scanning of an object. One such system provides for an array of electroacoustic transducers where the echo or return signals from the object under inspection are passed through individual lumped electromagnetic delay lines which can be appropriately designed to vary the time delay for each transducer, and thus provide an electronic focusing scheme. However, as a practical matter, the lumped time delay lines require a great deal of space and cumbersome switching circuits. Switching of this time delay system is controlled by a minicomputer, or microprocessor.

Other computer reconstruction techniques have been utilized in connection with acoustic imaging by other investigators. However, a number of practical problems exist, such as poor resolution of the image, and, most importantly, inability to provide for signal acquisition and reconstruction of the image in real time.

SUMMARY OF THE PRESENT INVENTION

The general objective of the present invention is to provide a real-time digital, synthetic-focus, acoustic imaging system which provides for acquisition of the desired signal and reconstruction of the image in less than 30 msecs., well above the rate required for real-time imaging; and, furthermore, provides high efficiency, excellent range and transverse resolution, and low sidelobe levels.

Generally, this objective is achieved by supplying a plurality of broadband pulses to an analog multiplexer, which in turn selects and delivers each pulse in sequence to one of a plurality of electroacoustic transducers arranged in a linear array so that acoustic waves generated by each transducer are directed through an acoustic propagating medium such as water or metal, to the object or area under investigation.

The echo, or return signal reflected from the object, is received by the same electroacoustic transducer for delivery of the multiplexer. Each signal is, in turn, delivered from the multiplexer to a preamplifier, and thereafter to an inverse filter which compensates for any deficiencies in the transducer itself, so that the effective transducer impulse response (the combined effect of transducer plus inverse filter) is as compact as possible (preferably a single sinusoid) within the bandwidth limitations of the overall system. While various inverse filter techniques previously known can be utilized, it is preferred, in accordance with one aspect of the present invention, to provide a programmable inverse filter which makes use of a hybrid digital-analog approach in order to achieve a 5 MHz bandwidth from a reliable low-cost design.

The shaped signal is then delivered from the filter to a nonlinear amplifier, preferably incorporating square root gain compression, which, in conjunction with the processing electronics and another nonlinear amplifier at the output, will provide a significant reduction in the sidelobe levels as well as an improvement in both range and transverse resolution of the ultimate image. Preferably, only a single amplifier handles all of the signals in sequence so that it can have excellent operating characteristics without particular regard for cost or complexity. The sequence of signals from the nonlinear amplifier, which, of course, are in analog form, and next converted by high speed analog-to-digital converter into a digital format, and these digital signals are, in turn, delivered to individual random access memory units wherein the signals are stored prior to further processing and reconstruction of the ultimate image.

Since, as will be obvious, a particular object or area under acoustic investigation will be spaced a different distance from each individual transducer in the array, a time differential in the receipt of the signals will exist, and, in accordance with another important aspect of the present invention, the time delay of the signals is automatically corrected as the stored digital signals are read out from their random access memory units to achieve a synthetic focus. Such focusing is accomplished by a programmed focus memory which, in turn, utilizes a number of random access memories which are pre-programmed from a computer utilizing information developed from the geometrical differences between the position of the object being investigated and each individual electroacoustic transducer. This information can be stored in the focus memory units in table form so that high speed reconstruction of the signals provides the ultimate image in real time.

The focused time-equalized signals in digital format are summed in a conventional digital adder and are then delivered to a digital-to-analog converter which provides an analog output signal which, after further amplification in a nonlinear amplifier, can be presented on a display unit such as a television display with a magnetically-deflected cathode ray tube.

As previously indicated, through the use of the high speed digital equipment, a real-time display in less than 30 msecs. is enabled with a 32 element transducer array system.

BRIEF DESCRIPTION OF THE DRAWINGS

The stated objective of the invention and the manner in which it is achieved as summarized hereinabove will be more readily understood by reference to the following detailed description of the embodiment of the invention illustrated in the accompanying drawings wherein FIG. 1 is a schematic block diagram of a digital, synthetic-focus acoustic imaging system embodying the present invention, FIG. 2 is an operational schematic illustrating the stages in the entire system operation, FIGS. 6a and 6b are graphical representations of the input and output signals of such inverse filter.

DETAILED DESCRIPTION OF THE EXEMPLARY EMBODIMENT OF THE INVENTION

With initial reference to FIG. 1, a pulse generator 10 is arranged to produce a series of broadband pulses. More particularly, the broadband pulses have a typical voltage of 50 volts and a length between 50 and 200 nsecs., in accordance with the center frequency of an acoustic transducer array to which they are delivered. As will be explained in more detail hereinafter, the pulses are kept short to enhance the definition or resolution of the entire imaging system, but on the other hand are sufficiently long so that, with the applied voltage, a readily observable signal can be obtained.

The broadband pulses are delivered to an analog multiplexer 12 which is arranged to deliver the pulses in ordered sequence to a number of like electro-acoustic transducer units 14 arranged in the mentioned longitudinal array, as generally indicated in FIG. 1, such units having a center frequency of approximately 3.5 MHz.

Figure 4:
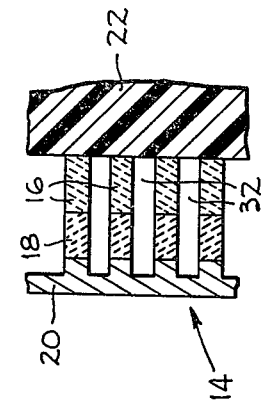
FIG. 4 is an enlarged fragmentary sectional view taken along line 4—4 of FIG. 3.
Figure 3:
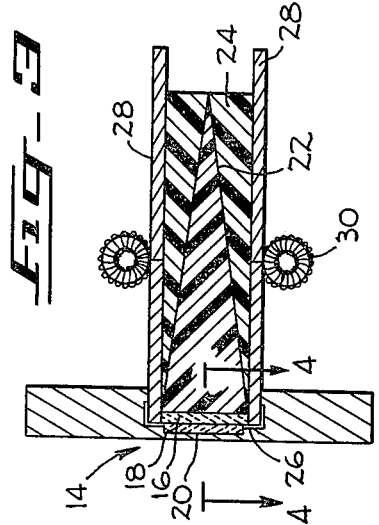
FIG. 3 is a cross-sectional view taken along line 3—3 of FIG. 1, showing details of a transducer array unit preferably utilized in the system of the invention.

As shown in more detail in FIGS. 3 and 4, the transducer array units 14 are highly efficient, each having a short duration impulse response and broad angular beamwidth; and for this purpose essentially tall and narrow piezoelectric ceramic elements 16 with quarter-wave matching layers are utilized. More particularly, the ceramic elements 16 are formed by a slab of piezoelectric ceramic material such as "PZT-5A" which is bonded to a silicon carbide-loaded epoxy backing 22 formed in a long wedge shape with a lossy flexible epoxy coating 24 around the edge to eliminate reflected signals from the backing. Electrical connection is made by brass leads 26 connected to the edges of the ceramic, and at their opposite extremities on mounted printed circuit boards 28, to impedance matching transformers 30 enabling the impedance of the transducer units 14 in the neighborhood of 750 ohms to be matched to the input standard 50-ohm impedance cables.

With additional reference particularly to FIG. 4, it will be seen that the individual ceramic elements 16 are separated by slots 32 which minimize the cross coupling between the transducer units 14 and thus achieve as broad angular beamwidth from each element as is possible.

As can be clearly shown by inspection of FIG. 4, the piezoelectric ceramic elements 16 have a height-to-width ratio in the order of 2 to 1, which allows for the excitation of a relatively pure piston-like extensional mode with a very high electromechanical coupling coefficient.

($K_T^2 = 0.47$ for PZT-5A).

To provide for good matching of acoustic energy into the adjacent low impedance load medium, which is typically water ($Z = 1.5 \times 10^6$ kg/m²-sec.), from the high acoustic impedance ceramic elements 16 ($Z = 29.7 \times 10^6$ kg/m²-sec.) over octave frequency bandwidths, quarter-wave acoustic matching layers are employed. Preferably, as shown, the first matching layer 18 is formed by a quarter-wave length piece of borosilicate glass and a second quarter-wave length matching layer 20 is formed from epoxy. The design provides a smooth frequency response which yields a short duration impulse response with a low insertion loss, and the ultimate transducer passband approaches the ideal of a gaussian-shaped band. While any number of transducer units 14 can be utilized in the transducer array, in the present instance 32 transducer units 14 as described hereinabove were utilized.

As each transducer unit 14 is excited by a pulse delivered through the analog multiplexer 12 from the pulse generator 10, an acoustic pulse is generated and propagates in generally cylindrical format, as indicated in FIG. 1, through an acoustic propagating medium 40 such as water to an object which is to be observed, and the reflected echo or signal is received by the same transducer unit for return through the analog multiplexer 12 where it preferably is initially amplified by a standard preamplifier unit 42.

Ideally, to provide optimum range and transverse resolution, the transducer response in the form of the reflected signal pulse should approximate a single sinusoid. As a practical matter, because of transducer deficiencies as well as amplitude distortions resultant from the signal propagating through an inhomogeneous medium, or poor contact between the transducer array and a substrate, the actual reflected signal waveform is substantially as shown in FIG. 6a at $S_{in}$.

In accordance with an important aspect of the present invention, an inverse filter 50 is utilized to process the signal pulse $S_{in}$, as shown in FIG. 6a to produce a filtered pulse $S_{out}$ of the form shown in FIG. 6b, approximating the ideal single sinusoid waveform. Generally, for this purpose, the inverse filter 50 will employ a tapped delay line with the signals from the tap being adjusted in amplitude and sign, and then added.

Such inverse filters can take various forms, examples being those described by Kerber, White and Wright in the 1976 IEEE Ultrasonic Symposium Proceedings, pages 577–581, entitled "S A W Inverse Filter for N D T" or the article entitled "Stationary and Non-Stationary Learning Characteristics of the L M S Adaptive Filter" by B. Widrow et al. in Proc. IEEE, Vol. 64, No. 8, pages 1151–1162 (August 1976); or preferably, the programmable filter diagrammatically indicated in FIG. 5, which makes use of a hybrid digital-analog approach in order to achieve a 5 MHz bandwidth in real time operation.

Figure 5:
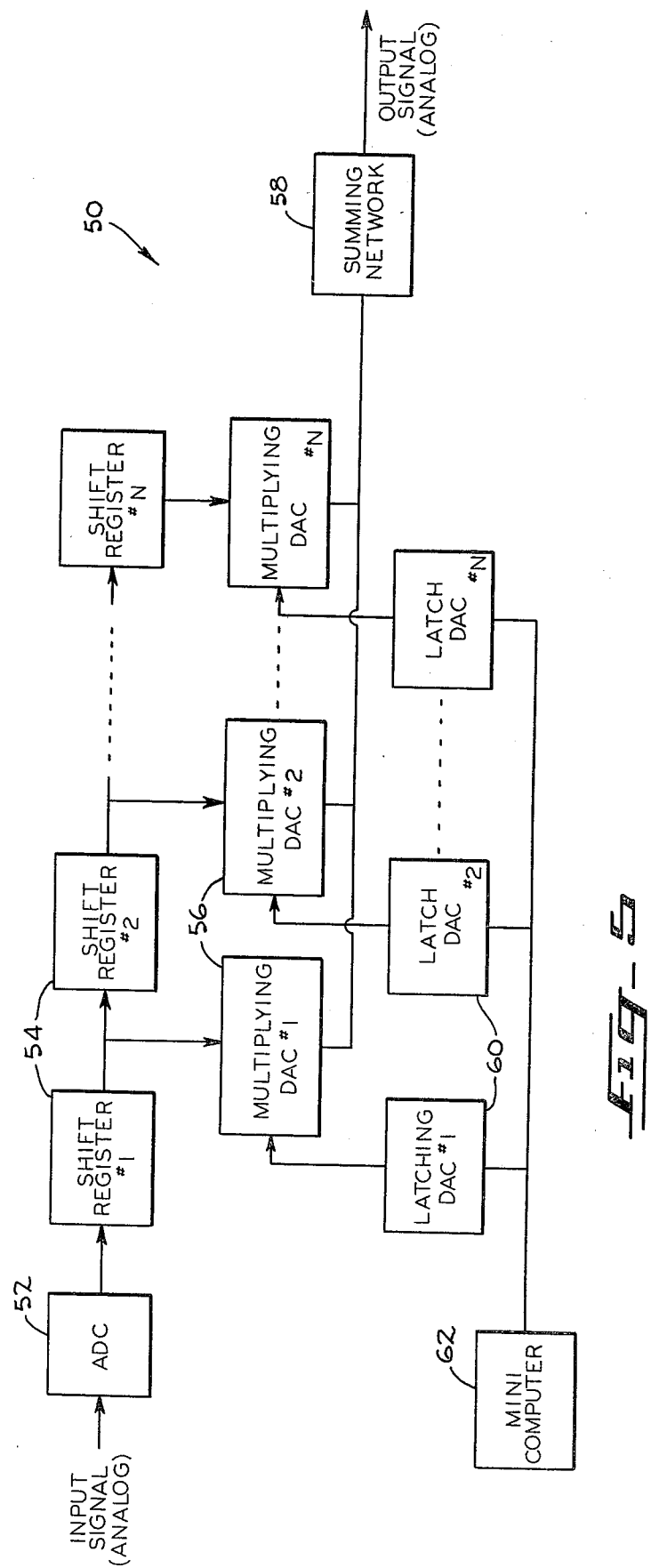
FIG. 5 is a detailed block diagrammatic view of the inverse filter utilized in the system.

More particularly, as shown in FIG. 5, the input signal as shown in FIG. 6a is delivered to an analog-to-digital converter (ADC) 52 which samples such signal and converts it into 8-bit digital words which are sequentially loaded into 8-bit wide digital shaft registers 54 which function as a tapped delay line. At each stage of the shift registers 54, a multiplying digital-to-analog converter (MDAC) 56 is used to multiply the digital word by an analog tap weight reference voltage to produce an analog current output. The outputs of all of the multiplying digital-to-analog converters 56 are added in a summing network 58 to provide the analog filter output in the form shown in FIG. 6b at $S_{out}$.

The multiplying reference voltages are established by a set of latching digital-to-analog converters (DAC) 60, which are programmed from a minicomputer 62 in accordance, preferably, with a Fourier transform technique which calculates in but a few seconds the Wiener filter solution desired. The LMS algorithm as used by Windrow can also be employed if desired to establish the requisite tap weight voltages.

If indeed the spectra of the input signal and the desired output signal are $X(\omega)$ and $D(\omega)$, the frequency response of the filter which gives the least mean-squared fit to the desired output signal in the presence of noise is given by the Wiener solution $$H(\omega) = \frac{D(\omega)X^*(\omega)}{X(\omega)X^*(\omega) + N^2(\omega)}$$

where $X^*(\omega)$ is the complex conjugate of $X(\omega)$ and
$N^2(\omega)$ is the noise power.

Once the requisite filter response has been calculated by whatever means, the filter is programmed and can operate in real time with a 5 MHz bandwidth and a 40 dB dynamic range.

After the received signal has been reduced to substantially a single cycle sinusoid $S_{out}$ by the inverse filter 50, such signal is delivered to a nonlinear amplifier 70 whose basic characteristics can be described by the formula $$V_{out} = \alpha \mathrm{signum}(V_{in})(|V_{in}|)^\beta$$

where $V_{out}$ is the output voltage of the amplifier,
$V_{in}$ is the input voltage,
$\alpha$ is the gain factor, and
$\beta$ is an exponent which is adjustable over a range from 0.25 up to 4, so that either gain compression or expansion can be provided.

In the present instance, $\beta$ is chosen as one half (square root), so that if one assumes that the ratio of the main lobe of a reflected signal to a side lobe is M, then, if one point on an object of amplitude a excites the main lobe and another point of amplitude b excites the side lobe, the ratio of their outputs normally will be Ma/b. If one takes the square root of the output of each transducer, the main lobe-to-side lobe ratio will still be M, but the ratio of the two outputs will be $M\sqrt{a/b}$. If we subsequently square the summed output of the ratio of the two signals, it will be $M^2 a/b$, and the original linear relation of the signals will be restored but the effect of the sidelobe levels will have changed from M to $M^2$, thus providing a consequent decrease in the sidelobe level by a factor of two in decibels, which obviously is of major importance for distinguishing or detecting a small target in close proximity to a large reflector.

A single nonlinear amplifier 70 incorporating the described gain compression can be utilized regardless of how many elements of the transducer array are to be used since, through the use of the described analog multiplexer 12, the signals from all of the individual transducer units 14 are delivered to the amplifier 70 in sequence. As a consequence of the fact that only a single nonlinear amplifier 70 is required at the input, this amplifier can be designed with little regard for its cost and complexity, and there will be no problems associated with matching the characteristics of a large number of nonlinear amplifiers such as might be encountered in a system which has an amplifier for every element of the transducer array.

In order to provide reconstruction of an image in real time from the signals received from the transducers 14, the signals from all the transducer units must be stored; and, in accordance with a critical aspect of the present invention, this requirement is achieved by using an ultrahigh speed analog-to-digital converter 80 with associated random access memory units (RAM) 90 correlated with the transducer units 14. More particularly, with continued reference to FIG. 1, the analog signals are delivered to the analog-to-digital converter 80 having a sampling or clock rate at a frequency of approximately 16 MHz to provide for precise conversion, such sampling rate being more than twice the upper cutoff frequency of the signals from the transducer array (5 MHz).

The digitized signals from the analog-to-digital converter 80 are then delivered selectively to respective random access memory units 90, it being understood that each signal memory unit has the same high speed clock rate of approximately 16 MHz.

The analog-to-digital converter 80, as mentioned, should have a clock or sampling rate at least twice the operating frequency of the transducer elements, and such requirement can be met readily by a commercial analog-to-digital converter such as the TRW TDC1007J A-to-D converter, which is capable of digitizing signals at up to a 30 MHz rate. Then, in turn, the random access memory units 90 capable of operating at the required high speed can consist of commercially available semi-conductor random access memory units such as the INTEL 2125-AL 1K×1 static RAM units arranged to provide 32 blocks of 1024 8-bit bytes of serial storage. These units are not described in further detail since they are commercially available and in and of themselves form no part of the invention; and those skilled in the art will recognize that various equivalent units can be utilized to perform desired signal acquisition, digitizing and storage functions.

The signal acquisition phase of the described system can be diagrammatically indicated by the schematic operation shown at the left of FIG. 2, where two objects $O_a$, $O_b$ to be imaged are positioned at different positions relative to the transducer array diagrammatically indicated at 14. The echoes or signal pulses reflected from these objects are shown at $S_a$ and $S_b$ in the memory diagram 100, it being notable that the signal positions on this time scale indicated from left to right on the memory section of the operational diagram vary with the particular position of each transducer element relative to the object. More particularly, if the distance from the particular object $O_a$ or $O_b$ is greater, it will be obvious that greater time for presentation of the reflected signal pulse will be necessitated, and is so indicated on the diagram.

The objects $O_a$ and $O_b$ can take the form of positive objects such as a piece of wire or the like, supported within an acoustic propagating medium such as water; and also may constitute, by way of example, a void in a piece of metal, or even a point of metallic stress therein, the reflected echo being dependent upon a discontinuity of some sort in the sensed area. It may be mentioned generally that acoustic imaging of the sort hereby envisioned has been used in many other applications such as diagnostic medical imaging, which has proved to be extremely successful, and the present invention is obviously applicable to such utilization.

The entire signal acquisition phase which has been thus far described takes no more than 10 msec., and reconstruction of the image, in accordance with the present invention, as will be explained hereinafter, takes but an additional 20 msec., so that real-time imaging in accordance with the primary objective of the present invention is readily achieved.

The signal pulses $S_a$ and $S_b$ each have time differentials as described above with reference to FIG. 2, and in order to reconstruct an image, it is necessary to provide equal time delays of the signals from all of the transducers 14 to the point or points of interest, in this case the objects $O_a$ and $O_b$. For this purpose, and to provide for the real-time reconstruction of the image, a focus memory 110 is utilized, which in the present instance takes the form of random access memory units which have been programmed in accordance with the geometrical differences of the paths between the individual transducer elements 14 and the point of interest.

Such information can be delivered into the focus memory 110 through a system controller unit 120 from the previously mentioned minicomputer 62 (or microprocessor), and thereafter can be retained as long as desired, or alternatively can be reprogrammed if a different array spacing, different field of view or imaging in alternate media are required. If, for example, a particular application is to be utilized, the reprogrammable random access memory units in the focus memory 110 can be replaced by programmable read-only memory units (PROM) which will simplify construction and reduce cost, but of course eliminate the possibility of reprogramming.

The system controller unit 120 is arranged to correlate introduction of time delay to the individual random access memory units 90, wherein the signals are stored with the vertical (Y) and horizontal (X) sweeps on an image display unit 130.

The format on the display unit 130 is a raster scanned image. In order to reconstruct a single line of that image, the signals in all 32 of the signal memory units 90 are read out in parallel and summed together in a digital adder 140. In order to achieve a focusing effect, the signals stored in each of the 32 signal memory units 90 must be read out at slightly different rates in accord with the distances between the individual transducer elements 14 and the image point being reconstructed. The focus memory 110 is arranged as 384 lines of 1024 bits per line. Focus steering logic indicated at 116 is employed to direct 32 of these 384 lines of focus information to the 32 signal memory units 90. Each line of focus information controls the rate at which the digital signal is read out of one of the signal memory units, effectively introducing the time delays required to reconstruct a line of the focused image. To reconstruct a different line of the image, the focus steering logic 116 selects a different set of 32 lines of focus information. The 384 lines of focus information contain all of the timing information required to reconstruct an entire 256 line raster scanned image.

After the required time delays have been introduced to the individual digital signals in the signal memory units 90 and these signals have been delivered to the digital adder 140, where they are summed to produce a digital output signal, such signal is thereafter reconverted into analog format by a conventional digital-to-analog converter 150. The output analog signal is delivered to a nonlinear amplifier 160 which provides for a squared gain expansion to make the output signal be correlated with the initial analog signal prior to its compression in the previously described nonlinear square root gain compression amplifier 70, so that a linear correlation between the input and output signal is established.

The output signal is arranged to provide for intensity modulation (Z) of the display unit 130 as mentioned, which preferably takes the form of a television monitor unit having a magnetic deflection cathode ray tube, although electrostatic deflection tubes such as used in conventional oscilloscopes can be utilized if necessary.

Operationally, the various time delays are indicated in FIG. 2 by the various indicia T1, T2, etc. It can be seen that at the display positions, $D_a$ and $D_b$, which correspond to the locations of the objects, $O_a$ and $O_b$, the signals from all of the transducer elements add together to give strong responses. The output signal modulates the intensity of the display so that two bright spots appear in the image to represent the two objects. A quantitative indication of the object size is also provided to enable the user to have general quantitative as well as positional information on the display unit. This system has demonstrated range and transverse resolutions of 0.5 mm. with low sidelobe levels.

Since, as previously indicated, the entire process is accomplished in approximately 30 msec., the reconstructed image can have a frame rate approximating 30 Hz, which is well above the rate required for real-time imaging; and, as a consequence, the user is provided not only with information having excellent resolution but also available for immediate use.

It will be apparent that many modifications and/or alterations in the particular structure described hereinabove can be made without departing from the spirit of the present invention, and the foregoing description of one embodiment is accordingly to be considered as purely exemplary and not in a limiting sense. As one obvious example, rather than the preferred electronic scan provided by the transducer array, a single transducer unit 14 can be used if mechanically scanned relative to the object, and can realize many features of the invention. Accordingly, the actual scope of the invention is to be indicated only by reference to the appended claims.

What is claimed is:

1. A real-time digital, synthetic-focus acoustic imaging system which comprises:
   an array of electro-acoustic transducers,
   a source of pulses,
   means arranged to selectively deliver pulses in sequence from said source to said transducers,
   means arranged to receive reflected signals in sequence from said transducers, an analog-to-digital converter for receiving and digitizing all signals from all of said transducers is sequence, digital memory means for receiving and storing the digitized signals from said analog-to-digital converter, focus memory means for equalizing the time delay of the digitized signals from all transducers, a single nonlinear amplifier providing square root compression gain arranged to amplify the signals received from each of said transducers before delivery to said analog-to-digital converter, means for adding all of said time-equalized digital signals to provide a summed digital output signal, a digital-to-analog converter arranged to receive said summed digital output signal to convert the same to an analog output signal, and a nonlinear amplifier for squared gain expansion of said output analog signal.

2. An inverse filter which comprises:

a plurality of shift registers arranged to operate as a tapped delay line when digital signals are received, a plurality of multiplying digital-to-analog converters connected to said shift registers to multiply the digital signals by tap weight reference voltages to produce an analog current output, and means for delivering said reference voltages to said digital-to-analog converters including a plurality of latching digital-to-analog converters, and means for programming said latching digital-to-analog converters in accordance with the desired frequency response in accord with the Wiener solution $$H(\omega) = \frac{D(\omega)X^*(\omega)}{X(\omega)X^*(\omega) + N^2(\omega)}$$

where $X(\omega)$ is the input signal, $X^*(\omega)$ is the complex conjugate of $X(\omega)$, $N^2(\omega)$ is the noise power, and $D(\omega)$ is the desired output signal, and means for summing the output currents and converting to a single output voltage signal.

3. A real-time digital, synthetic-focus acoustic imaging system which comprises:

an array of electro-acoustic transducers, a source of pulses, means arranged to selectively deliver pulses in sequence from said source to said transducers, means arranged to receive reflected signals in sequence from said transducers, an analog-to-digital converter for receiving and digitizing all signals from all of said transducers in sequence, digital memory means for receiving and storing the digitized signals from said analog-to-digital converter, focus memory means for equalizing the time delay of the digitized signals from all transducers, and an inverse filter arranged to process each signal from said signal receiving means to provide a filtered output signal having the format of substantially a single sinusoid.

4. A real-time digital, synthetic-focus acoustic imaging system according to claim 3 wherein:

said inverse filter has a frequency response given by the Wiener solution $$H(\omega) = \frac{D(\omega)X^*(\omega)}{X(\omega)X^*(\omega) + N^2(\omega)}$$

where $X(\omega)$ is the actual transducer impulse response, $X^*(\omega)$ is the complex conjugate of $X(\omega)$, $N^2(\omega)$ is the noise power, and $D(\omega)$ is the desired output.

* * * * *